United States Patent
Haase

(10) Patent No.: US 10,765,571 B2
(45) Date of Patent: Sep. 8, 2020

(54) TAMPON DISPOSING SYSTEM

(71) Applicant: Eryca Haase, Springfield, MA (US)

(72) Inventor: Eryca Haase, Springfield, MA (US)

(*) Notice: Subject to any disclaimer, the term of this patent is extended or adjusted under 35 U.S.C. 154(b) by 0 days.

(21) Appl. No.: 16/419,681

(22) Filed: May 22, 2019

(65) Prior Publication Data

US 2019/0350777 A1 Nov. 21, 2019

Related U.S. Application Data

(60) Provisional application No. 62/674,147, filed on May 21, 2018.

(51) Int. Cl.
*A61F 13/551* (2006.01)

(52) U.S. Cl.
CPC ........... *A61F 13/5518* (2013.01); *A61F 2013/55195* (2013.01)

(58) Field of Classification Search
CPC .................. A61F 13/5518; A61F 2013/55195
USPC ............ 206/438, 440, 441, 581; 604/385.01, 604/385.02
See application file for complete search history.

(56) References Cited

U.S. PATENT DOCUMENTS

| | | | | |
|---|---|---|---|---|
| 7,073,666 B2* | 7/2006 | Arndt | ................ | A61F 13/55185 206/438 |
| 8,991,610 B2* | 3/2015 | Kuroda | ............... | A61F 13/5514 206/581 |
| 9,186,284 B1* | 11/2015 | Hernandez | ........ | A61F 13/55145 |
| 2005/0098466 A1* | 5/2005 | Thomas | .............. | A61F 13/5518 206/440 |
| 2010/0249742 A1* | 9/2010 | McConnell | ......... | A61F 13/5518 604/385.02 |
| 2010/0320115 A1* | 12/2010 | Perry | ................ | A61F 13/55175 206/581 |
| 2013/0319890 A1* | 12/2013 | Davis | .................. | A61F 13/5518 206/440 |
| 2014/0276522 A1* | 9/2014 | Thompson | .......... | A61F 13/5518 604/385.02 |
| 2015/0257949 A1* | 9/2015 | Thompson | .......... | A61F 13/5518 383/105 |
| 2018/0028373 A1* | 2/2018 | Donovan | .......... | A61F 13/55185 |

* cited by examiner

*Primary Examiner* — Luan K Bui
(74) *Attorney, Agent, or Firm* — The Iwashko Law Firm, PLLC; Lev Ivan Gabriel Iwashko

(57) ABSTRACT

A tampon disposing system, including a tampon, a wrapper to encase the tampon therein, and a bag attached to an inner side portion of the wrapper to store the tampon and at least a portion of the wrapper therein.

4 Claims, 1 Drawing Sheet

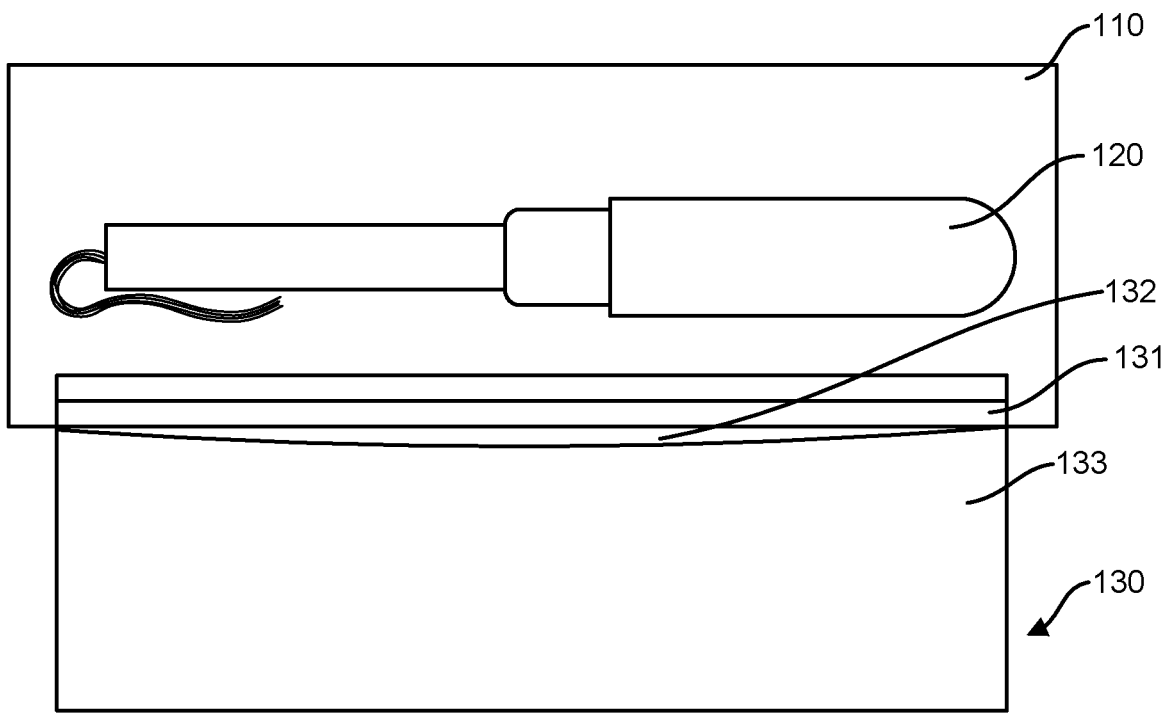

TAMPON DISPOSING SYSTEM

This application claims the benefit of, and incorporates by reference, U.S. provisional patent application Ser. No. 62/674,147, entitled "Tampon Disposing Bag," which was filed on May 21, 2018.

BACKGROUND

1. Field

The present general inventive concept relates generally to a tampon disposing bag.

2. Description of the Related Art

When it comes to menstrual health, many products are starting to be produced in the market intended to ease any struggles a menstruating person may have throughout their cycle, including making tampons that are more portable. However, there has yet to emerge any product that aids with the discreet disposal of used tampons that reduces hassle and does not interfere with septic tanks.

Therefore, there is a need for a system that facilitates disposal of tampons in an environmentally-safe manner.

SUMMARY

The present general inventive concept provides a bag to facilitate disposal of a tampon.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a tampon disposal system, including a tampon, a wrapper to encase the tampon therein, and a bag attached to an inner side portion of the wrapper to store the tampon and at least a portion of the wrapper therein.

The bag may include an attachment portion to attach to the inner side portion of the wrapper with an adhesive, a storage portion to store the wrapper and the tampon therein, and an opening to allow the wrapper and the tampon to enter the storage portion.

The bag and the tampon may be disposed within the wrapper when the wrapper is sealed.

The foregoing and/or other features and utilities of the present general inventive concept may also be achieved by providing a tampon disposal system, including a tampon, a wrapper to encase the tampon therein, such that the tampon is fully enveloped by the wrapper, a bag attached to the wrapper to store the tampon and at least a portion of the wrapper therein. 1.53

BRIEF DESCRIPTION OF THE DRAWINGS

These and/or other features and utilities of the present generally inventive concept will become apparent and more readily appreciated from the following description of the embodiments, taken in conjunction with the accompanying drawings of which:

FIG. 1 illustrates a tampon disposal system, according to an exemplary embodiment of the present general inventive concept.

DETAILED DESCRIPTION

Various example embodiments (a.k.a., exemplary embodiments) will now be described more fully with reference to the accompanying drawings in which some example embodiments are illustrated. In the FIGURES, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

FIG. 1 illustrates a tampon disposal system 100, according to an exemplary embodiment of the present general inventive concept.

The tampon disposal system 100, and components thereof, may be constructed from cloth, cotton, polyester, threads, string, metal, plastic, rubber, wood, or any other material known to one of ordinary skill in the art, and may be made from bio-degradable material.

The tampon disposal system 100 may include a wrapper 110, a tampon 120, and a bag 130, but is not limited thereto.

The wrapper 110 may have various shapes and sizes, and may have a substantially rectangular shape, but is not limited thereto. The wrapper 110 may be designed to hold the tampon 120 and the bag 130 therein. In other words, the bag 130 and the tampon 120 may be disposed within the wrapper 110 when the wrapper 110 is sealed, i.e., unopened.

The tampon 120 may include a tampon, an applicator, a string, and any other portion of a tampon known to one of ordinary skill in the art.

The bag 130 may include an attachment portion 131, an opening 132, and a storage portion 133.

The bag 130 may be attached to an inner side portion of the wrapper 110 via the attachment portion 131, which may be a side portion of the bag 130 that is adhered to the side portion of the wrapper 110.

The opening 132 may allow a user to place a used tampon within the storage portion 133 of the bag 130.

As such, after the user opens the wrapper 110 to expose the tampon 120 and the bag 130, the user may extract a used tampon from her vagina, place the used tampon into the storage portion 133 of the bag 130 via the opening 132, and then place the tampon 120 into her vagina.

The wrapper 110 and any unused portion of the tampon 120 (e.g., an applicator) may also be inserted into the storage portion 133 of the bag 130 via the opening 132, and then the bag 130 (along with the wrapper 110, any unused portion of the tampon 120, and the used tampon) may be thrown away or flushed.

As such, a woman can avoid touching a used tampon with her hands.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A tampon disposing system, comprising:
   a tampon;
   a wrapper to encase the tampon therein; and
   a bag attached to an inner side portion of the wrapper to store the tampon and at least a portion of the wrapper therein, the bag comprising:
      an opening disposed outside a boundary of the wrapper.

2. The tampon disposing system of claim 1, wherein the bag further comprises:
   an attachment portion to attach to the inner side portion of the wrapper with an adhesive; and
   a storage portion to store the wrapper and the tampon therein.

3. The tampon disposing system of claim 1, wherein the bag and the tampon are disposed within the wrapper when the wrapper is sealed.

4. A tampon disposing system, comprising:
   a tampon;
   a wrapper to encase the tampon therein, such that the tampon is fully enveloped by the wrapper;
   a bag attached at least partially within the wrapper to store the tampon and at least a portion of the wrapper therein, such that an opening of the bag is disposed outside a boundary of the wrapper.

* * * * *